(12) United States Patent
Hoshi

(10) Patent No.: US 6,194,351 B1
(45) Date of Patent: Feb. 27, 2001

(54) HERBICIDAL COMPOSITION

(75) Inventor: Hisayuki Hoshi, Toyonaka (JP)

(73) Assignee: Sumitomo Chemical Company, Limited, Osaka (JP)

(*) Notice: Subject to any disclaimer, the term of this patent is extended or adjusted under 35 U.S.C. 154(b) by 0 days.

(21) Appl. No.: 09/274,491

(22) Filed: Mar. 23, 1999

(30) Foreign Application Priority Data

Mar. 26, 1998 (JP) .................................................. 10-079030

(51) Int. Cl.[7] .............................. A01N 57/00; A01N 43/36

(52) U.S. Cl. ........................... 504/128; 504/127; 504/138

(58) Field of Search .................................... 504/127, 128, 504/138

(56) References Cited

U.S. PATENT DOCUMENTS

| | | | |
|---|---|---|---|
| 5,045,105 | 9/1991 | Grossmann et al. | 71/74 |
| 5,062,884 | 11/1991 | Plath et al. | 71/95 |

*Primary Examiner*—Allen J. Robinson
(74) *Attorney, Agent, or Firm*—Birch, Stewart, Kolasch and Birch, LLP

(57) ABSTRACT

The present invention provides for pesticidal compositions comprising (i) at least one compound selected from the group consisting of N-(phosphonomethyl)glycine, a salt thereof and ammonium-DL-homoalanin-4-yl(methyl) phosphinate, and (ii) ethyl 2-chloro-3-[2-chloro-5-(1,3-dioxo-4,5,6,7-tetrahydroisoindolin-2-yl)phenyl]acrylate as active ingredients. The present inventive compositions can control a wide variety of weeds in corn fields, soybean fields, wheat fields, barley fields, oat fields, rye fields, rice fields, paddy fields or the like, with selectivity to crops. Methods for controlling weeds are also provided.

12 Claims, No Drawings

HERBICIDAL COMPOSITION

FIELD OF THE INVENTION

The present invention relates to a herbicidal composition.

BACKGROUND OF THE INVENTION

Currently, various herbicides are being utilized, but since there are various weeds that are target of control, and because the growth thereof continues for a long time, a herbicide that has a higher herbicidal activity, a quicker appearance of herbicidal effect, a wider herbicidal spectrum and a safety for crops is desired.

SUMMARY OF THE INVENTION

The present inventor has intensely studied to seek out an excellent herbicide, and has found that by applying a herbicidal composition which comprises, as active ingredients, (i) at least one compound selected from the group consisting of N-(phosphonomethyl)glycine (common name: glyphosate, hereinafter, referred to as glyphosate), a salt thereof and ammonium-DL-homoalanin-4-yl(methyl)phosphinate (common name: glufosinate-ammonium, hereinafter, referred to as glufosinate-ammonium), and (ii) ethyl 2-chloro-3-[2-chloro-5-(1,3-dioxo-4,5,6,7-tetrahydroisoindolin-2-yl)phenyl]acrylate (common name: cinidon-ethyl, hereinafter, referred to as cinidon-ethyl), various weeds that emerge or grow in crop-lands or non-crop-lands can be controlled effectively, and that the herbicidal effect produced thereby is synergistically increased as compared with the cases where the active ingredients are independently used. As such, the provided herbicidal composition can, therefore, be applied at a low amount. Moreover, by utilizing the inventive herbicidal compositions, the time necessary for appearance of a herbicidal effect can be shortened, a broadened weed control spectrum can be achieved and a wide variety of weeds can be controlled selectively, without producing problems of phytotoxicity against crops such as corn, soybean, wheat, barley, oat, rye and rice. Accordingly, the present invention has been obtained.

DETAILED DESCRIPTION OF THE INVENTION

The present invention provides a herbicidal composition that comprises, as active ingredients, (i) at least one selected from the group consisting of glyphosate, a salt thereof and glufosinate-ammonium, and (ii) cinidon-ethyl.

Glyphosate, the salt thereof and glufosinate-ammonium are compounds described in Farm Chemicals Handbook, 1995(established by Meister Publishing Co., 1995) page C188 and C189. The term "salt" in the context of the present invention means all the agriculturally acceptable salts, and isopropylamine salt, ammonium salt sodium salt and the like can be exemplified.

Cinidon-ethyl is a compound described in JP-62-185071-A.

The present inventive herbicidal compositions are excellent as herbicides because they have a herbicidal activity against a wide variety of weeds with good selectivity between weeds and crops, and they exhibit an excellent herbicidal activity in no-till cultivation and non-agricultural fields as well as in till cultivation.

The present inventive herbicidal compositions have a herbicidal activity against the following variations of weeds that cause a problem for crops in fields of corn, soybean, wheat, barley, oat, rye or rice.

Polygonaceous weeds:
wild buckwheat (*Polygonum convolvulus*), pale smartweed (*Polygonum lapathifolium*), pennsylvania smartweed (*Polygonum pensylvanicum*), ladysthumb (*Polygonum persicaria*), curly dock (*Rumex crispus*), broad leaf dock (*Rumex obtusifolius*) and Japanese knotweed (*Polygonum cuspidatum*);
Portulacaceous weeds:
common purslane (*Portulaca oleracea*);
Caryophyllaceous weeds:
common chickweed (*Stellaria media*);
Chenopodiaceous weeds:
common lambsquarters (*Chenopodium album*) and kochia (*Kochia scoparia*).
Amaranthaceous weeds:
redroot pigweed (*Amaranthus retroflexus*) and smooth pigweed (*Amaranthus hybridus*);
Cruciferous (*brassicaceous*) weeds:
wild radish (*Raphanus raphabistrum*), wild mustard (*Sinapis arvensis*) and Shepherds purse (*Capsella bursa-pastoris*);
Leguminous (*fabaceous*) weeds:
hemp sesbania (*Sesbania exaltata*), sicklepod (*Cassia obtusifolia*), Florida beggarweed (*Desmodium tortuosum*), and white clover (*Trifolium repens*);
Malvaceous weeds:
velvetleaf (*Abutilon theophrasti*) and prickly sida (*Sida spinosa*);
Violaceous weeds:
field pansy (*Viola arvensis*) and wild pansy (*Viola tricolor*);
Rubiaceous weeds:
catchweed bedstraw (*Galium aparine*);
Convolvulaceous weeds:
ivyleaf morningglory (*Ipomoea hederacea*), tall morningglory (*Ipomoea purpure*), entireleaf morningglory (*Ipomoea hederacea* var. integriuscula), pitted morningglory (*Ipomoea lacunosa*) and field bindweed (*Convolvulus arvensis*);
Labiate weeds:
red deadnettle (*Lamium purpureum*) and henbit (*Lamium amplexicaure*);
Solanaceous weeds:
imsonweed (*Datura stramonium*) and black nightshade (*Solanum nigrum*);
Scrophulariaceous weeds:
Persian speedwell (*Veronica persica*) and Ivyleaf speedwell (*Veronica hederifolia*);
Composite weeds:
common cocklebur (*Xanthium pensylvanicum*), common sunflower (*Helianthus annuus*), scentless chamomile (*Matricaria perforata* or *inodora*), corn marigold (*Chrysanthemum segetum*), pineappleweed (*Matricaria matricarioides*), common ragweed (*Ambrosia artemisiifolia*), giant ragweed (*Ambrosia trifida*), Mare'stail (*Erigeron canadensis*), *Artemisia princeps, Solidago altissima;*
Boraginaceous weeds:
forget-me-not (*Myosotis arvensis*)
Asclepiadaceous weeds:
common milkweed (*Asclepias syriaca*)
Euphorbiaceous weeds:
sun spurge (*Euphorbia helioscopia*) and spotted spurge (*Euphorbia maculata*).
Graminaceous weeds:
barnyardgrass (*Echinochloa crus-galli*), green foxtail (*Setaria viridis*), giant foxtail (*Setaria faberi*), large crabgrass (*Digitaria sanguinalis*), goosegrass (*Eleusine* indica), annual bluegrass (*Poa annua*), blackgrass (*Alopecurus myosuroides*), wild oats (*Avena fatua*), johnsongrass (*Sorghum halepense*), quackgrass (*Agropyron repens*), downy brome (*Bromus tectorum*), Bermudagrass (*Cynodon dactylon*), fall panicum (*Panicum dichotomiflorum*), *Panicum texanum* and shattercane (*Sorghum vulgare*);

Commelinaceous weeds:

common dayflower (*Commelina communis*)

Equisetaceous weeds:

field horsetail (*Equisetum arvense*);

Cyperaceous weeds:

rice flatsedge (*Cyperus iria*), purple nutsedge (*Cyperus rotundus*) and yellow nutsedge (*Cyperus esculentus*).

At the same time, the present composition exhibits no significant phytotoxicity on crops such as corn, soybean, wheat, barley, oat, rye and rice.

When the present composition is used in paddy fields, it may be sprayed to foliage of weeds in a preplant burndown application before flooding, or after seeding rice it may be sprayed to foliage of weeds in a delayed pre-emergence application before flooding, preferably.

The present composition effectively exhibits an excellent herbicidal activity on weeds, e.g., dicotyledonous plants such as hemp sesbania (*Sesbania exaltata*), ivyleaf morningglory (*Ipomoea hederacea*), tall morningglory (*Pharbitis purpurea*), entireleaf morningglory (*Ipomoea hederacea* var. integriuscula), pitted morningglory (*Ipomoea lacunosa* L.), common cocklebur (*Xanthium pensylvanicum*), and pensylvania smartweed (*Polygonum pensylvanicum*); and monocotyledonous plants such as barnyardgrass (*Echinochloa crus-galli*), southern crabgrass (*Digitaria ciliaris*), goosegrass (*Eleusine indica*), sprangletop (*Leptochloa chinensis*), broadleaf signaigrass (*Brachiaria platyphylla*), umbrella sedge (*Cyperus difformis*), and rice flatsedge (*Cyperus iria*), while it exhibits no significant phytotoxicity on rice.

The crops for the present invention also include crops that were granted a tolerance, utilizing conventional breeding or genetic engineering methods, against glyphosate, a salt thereof or glufosinate-ammonium. For genetic engineering methods to make crops that are tolerant against glyphosate, a salt thereof or glufosinate-ammonium, the details thereof are described in WO 86/2097, WO 87/5627, WO 9214449, U.S. Pat. No. 4,971,908, U.S. Pat. No. 5,145,783, U.S. Pat. No. 5,510,471, U.S. Pat. No. 5,633,448, EP-257542-A and EP-275957-A.

For the present composition, the mixing ratio of the compound(s) selected from the group consisting of glyphosate, a salt thereof or glufosinate-ammonium to cinidon-ethyl for active ingredients, may vary with the species of weeds to be controlled, the situation of application, conditions of application and the like, but is usually in the range of about 0.5:1 to 500:1 by weight, preferably in the range of about 2:1 to 100:1 by weight.

The present composition is usually utilized after formulating into emulsifiable concentrates, wettable powders, flowables, granules or the like by mixing a solid carrier(s), liquid carrier(s), or the like, and when necessary, adding surfactant(s) or other adjuvants for formulation. The formulations thereof generally comprise (i) at least one compound selected from the group consisting of glyphosate, a salt thereof and glufosinate-ammonium and (ii) cinidon-ethyl in a total amount of about 0.5 to 90% by weight, and preferably about 1 to 80% by weight.

In an event of formulation, as the utilized solid carrier, examples include fine powders or granules of clays (e.g., kaolinite, diatomaceous earth, synthetic hydrated silicon oxide, Fubasami clay, bentonite, acid clay), talc and other inorganic minerals (e.g., sericite, powdered quartz, powdered sulfur, activated carbon, calcium carbonate), and chemical fertilizers (e.g., ammonium sulfate, ammonium phosphate, ammonium nitrate, ammonium chloride, urea); and as the liquid carrier, examples include water, alcohols (e.g., methanol, ethanol), ketones (e.g., acetone, methyl ethyl ketone, cyclohexanone), aromatic hydrocarbons (e.g., toluene, xylene, ethylbenzene, methylnaphthalene), non-aromatic hydrocarbons (e.g., hexane, cyclohexane, kerosine), esters (e.g., ethyl acetate, butyl acetate), nitriles (e.g., acetonitrile, isobutyronitrile), ethers (e.g., dioxane, diisopropyl ether), acid amides (e.g., dimethylformamide, dimethylacetamide), and halogenated hydrocarbons (e.g., dichloroethane, trichloroethylene).

As the surfactant, examples include alkylsulfic esters, alkylsulfonic salts, alkylarylsulfonic salts, alkyl aryl ethers and their polyoxyethylene derivatives, polyethylene glycol ethers, polyhydric alcohol esters and sugar alcohol derivatives.

As the other adjuvants for formulation, examples include adhesive agents or dispersing agents, such as casein, gelatin, polysaccharides (e.g., starch, gum arabic, cellulose derivatives, alginic acid), lignin derivatives, bentonite, and synthetic water-soluble polymers (e.g., polyvinyl alcohol, polyvinyl pyrrolidone, polyacrylic acid); and stabilizers such as PAP (isopropyl acid phosphate), BHT (2,6-tert-butyl-4-methylphenol), BHA (2-/3-tert-butyl-4-methoxyphenol), vegetable oils, mineral oils, fatty acids, and fatty acid esters.

The present inventive compositions can also be prepared by formulating each of the active ingredients by the formulation methods as described above, and then mixing these formulations together.

The present inventive compositions formulated in the above manner may be applied to plants by itself (i.e., as it is) or with a dissolving thereof in water. The present composition may further be utilized by mixing with other herbicide(s) to provide an enhancement in herbicidal activity, and further they may be utilized in combination with insecticides, bactericides, fungicides, plant growth regulators, fertilizers, safeners or soil conditioners.

The application amount of the present inventive compositions may vary with the mixing rate of the at least one compound selected from the group consisting of glyphosate, a salt thereof and glufosinate-ammonium to cinidon-ethyl, weather conditions, formulation, application timing, application method, application location, objective weed to be controlled or objective crop to be protected, but the total amount of the active ingredient compounds applied per 1 hectare with the inventive compositions is usually from about 100 to 10,000 g, and preferably from about 200 to 2000 g. Emulsifiable concentrates, wettable powders, flowables or the like are applied after diluting the predetermined amount per 1 hectare with about 100 to 1000 L of water.

Hereinafter, the formulation examples are given. Parts represents parts by weight in the examples below.

FORMULATION EXAMPLE 1

Five (5) parts of cinidon-ethyl, 25 parts of glyphosate or a salt thereof, 3 parts of calcium ligninsulfonate, 2 parts of sodium laurylsulfate and 65 parts of synthetic hydrated silicon oxide are well pulverized and mixed to obtain each wettable powder.

FORMULATION EXAMPLE 2

Two-fifths (0.4) part of cinidon-ethyl, 40 parts of glyphosate or a salt thereof, 3 parts of calcium ligninsulfonate, 2 parts of sodium laurylsulfate and 54.6 parts of synthetic hydrated silicon oxide are well pulverized and mixed to obtain each wettable powder.

FORMULATION EXAMPLE 3

Twenty (20) parts of cinidon-ethyl, 40 parts of glyphosate or a salt thereof, 3 parts of calcium ligninsulfonate, 2 parts of sodium laurylsulfate and 35 parts of synthetic hydrated silicon oxide are well pulverized and mixed to obtain each wettable powder.

FORMULATION EXAMPLE 4

One-half (0.5) part of cinidon-ethyl, 10 parts of glyphosate or a salt thereof, 3 parts calcium of ligninsulfonate, 2 parts of sodium laurylsulfate and 84.5 parts of synthetic hydrated silicon oxide are well pulverized and mixed to obtain each wettable powder.

FORMULATION EXAMPLE 5

Five (5) parts of cinidon-ethyl, 25 parts of glyphosate or a salt thereof, 3 parts of polyoxyethylene sorbitan monooleate, 3 parts of CMC (carboxymethyl cellulose) and 64 parts of water are mixed and wet pulverized until the particle size thereof is 5 microns or smaller, to thereby obtain a flowable.

FORMULATION EXAMPLE 6

Two-fifths (0.4) part of cinidon-ethyl, 40 parts of glyphosate or a salt thereof, 3 parts of polyoxyethylene sorbitan monooleate, 3 parts of CMC (carboxymethyl cellulose) and 53.6 parts of water are mixed and wet pulverized until the particle size thereof is 5 microns or smaller, to thereby obtain a flowable.

FORMULATION EXAMPLE 7

Twenty (20) parts of cinidon-ethyl, 40 parts of glyphosate or a salt thereof, 3 parts of polyoxyethylene sorbitan monooleate, 3 parts of CMC (carboxymethyl cellulose) and 34 parts of water are mixed and wet pulverized until the particle size thereof is 5 microns or smaller, to thereby obtain a flowable.

FORMULATION EXAMPLE 8

One-half (0.5) part of cinidon-ethyl, 10 parts of glyphosate or a salt thereof, 3 parts of polyoxyethylene sorbitan monooleate, 3 parts of CMC (carboxymethyl cellulose) and 83.5 parts of water are mixed and wet pulverized until the particle size thereof is 5 microns or smaller, to thereby obtain a flowable.

FORMULATION EXAMPLE 9

Ten (10) parts of cinidon-ethyl, 25 parts of glufosinate-ammonium, 3 parts of calcium ligninsulfonate, 2 parts of sodium laurylsulfate and 60 parts of synthetic hydrated silicon oxide are well pulverized and mixed to obtain a wettable powder.

FORMULATION EXAMPLE 10

Two-fifths (0.4) part of cinidon-ethyl, 40 parts of glufosinate-ammonium, 3 parts of calcium ligninsulfonate, 2 parts of sodium laurylsulfate and 54.6 parts of synthetic hydrated silicon oxide are well pulverized and mixed to obtain a wettable powder.

FORMULATION EXAMPLE 11

Twenty (20) parts of cinidon-ethyl, 20 parts of glufosinate-ammonium, 3 parts of calcium ligninsulfonate, 2 parts of sodium laurylsulfate and 55 parts of synthetic hydrated silicon oxide are well pulverized and mixed to obtain a wettable powder.

FORMULATION EXAMPLE 12

One (1) part of cinidon-ethyl, 10 parts of glufosinate-ammonium, 3 parts of calcium ligninsulfonate, 2 parts of sodium laurylsulfate and 84 parts of synthetic hydrated silicon oxide are well pulverized and mixed to obtain a wettable powder.

FORMULATION EXAMPLE 13

Ten (10) parts of cinidon-ethyl, 25 parts of glufosinate-ammonium, 3 parts of polyoxyethylene sorbitan monooleate, 3 parts of CMC (carboxymethyl cellulose) and 59 parts of water are mixed and wet pulverized until the particle size thereof is 5 microns or smaller, to thereby obtain a flowable.

FORMULATION EXAMPLE 14

Two-fifths (0.4) part of cinidon-ethyl, 40 parts of glufosinate-ammonium, 3 parts of polyoxyethylene sorbitan monooleate, 3 parts of CMC (carboxymethyl cellulose) and 53.6 parts of water are mixed and wet pulverized until the particle size thereof is 5 microns or smaller, to thereby obtain a flowable.

FORMULATION EXAMPLE 15

Twenty (20) parts of cinidon-ethyl, 20 parts of glufosinate-ammonium, 3 parts of polyoxyethylene sorbitan monooleate, 3 parts of CMC (carboxymethyl cellulose) and 54 parts of water are mixed and wet pulverized until the particle size thereof is 5 microns or smaller, to thereby obtain a flowable.

FORMULATION EXAMPLE 16

One (1) part of cinidon-ethyl, 10 parts of glufosinate-ammonium, 3 parts of polyoxyethylene sorbitan monooleate, 3 parts of CMC (carboxymethyl cellulose) and 83 parts of water are mixed and wet pulverized until the particle size thereof is 5 microns or smaller, to thereby obtain a flowable.

Hereinafter, the test examples are given.
Evaluation Criteria

The herbicidal activity is evaluated at 11 levels with indices of 0 to 10, i.e., shown by numeral "0", "1", "2", "3", "4", "5", "6", "7", "8", "9", or "10", wherein "0" means that there was no or little difference in the degree of germination or growth between the treated plants and the untreated plants at the time of evaluation, and "10" means that the test plants died completely or their germination or growth was completely inhibited.

TEST EXAMPLE 1

Plastic pots each having an area of 26.5×19 $cm^2$ and a depth of 7 cm were filled with upland soil, then seeded with giant foxtail (*Setaria faberi*), barnyardgrass (*Echinochloa crus-galli*), johnsongrass (*Sorghum halepense*), common lambsquarters (*Chenopodium album*), common ragweed (*Ambrosia artemisiifolia*), common cocklebur (*Xanthium strumarium*) and ivyleaf morningglory (*Ipomoea*

*hederacea*) (hereinafter abbreviated, in order, within Table 1 below, as AE, IB, SM, SI, BK, OM and AA), and were grown for 25 days in a greenhouse.

A cinidon-ethyl emulsifiable concentrate obtained by mixing together well 10 parts cinidon-ethyl, 14 parts polyoxyethylene styrylphenyl ether, 6 parts calcium dodecylbenzenesulfonate, 35 parts of xylene and 35 parts cyclohexanone, a formulated glyphosate product (trade name: Roundup; seller, Monsanto Japan Limited; distributor, Sankyo Co., Ltd.; it comprises glyphosate isopropyl amine salt) and a mixture of said cinidon-ethyl emulsifiable concentrate and said formulated glyphosate product were independently diluted in their prescribed amounts with water, and then uniformly sprayed over the test plants with a small sprayer. After the application, the test plants were grown in the greenhouse for 5 days, and the herbicidal activity was then examined. The results are given in Table 1.

TABLE 1

| Examined Compound | Dosage (g/ha) | Herbicidal Activity | | | | | | |
|---|---|---|---|---|---|---|---|---|
| | | AE | IB | SM | SI | BK | OM | AA |
| Cinidon-ethyl | 80 | 3 | 3 | 3 | 5 | 8 | 7 | 7 |
| Glyphosate | 560 | 1 | 1 | 1 | 0 | 0 | 0 | 0 |
| Cinidon-ethyl and Glyphosate | 80 + 560 | 6 | 7 | 7 | 7 | 10 | 10 | 10 |

TEST EXAMPLE 2

Plastic pots each having an area of 26.5×19 cm$^2$ and a depth of 7 cm were filled with upland soil, then seeded with giant foxtail (*Setaria faberi*), barnyardgrass (*Echinochloa crus-galli*), johnsongrass (*Sorghum halepense*) (hereinafter abbreviated, in order, in Table 2, below, as AE, IB or SM), and were grown for 25 days in a greenhouse.

A cinidon-ethyl emulsifiable concentrate obtained by mixing together well 10 parts cinidon-ethyl, 14 parts polyoxyethylene styrylphenyl ether, 6 parts calcium dodecylbenzenesulfonate, 35 parts of xylene and 35 parts cyclohexanone, a formulated glufosinate-ammonium product (trade name: basta; seller, Basta Association Department; distributor, Hoechst Japan Company Ltd.) and a mixture of said cinidon-ethyl emulsifiable concentrate and said formulated glufosinate-ammonium product were independently diluted in their prescribed amounts with water, and then uniformly sprayed over the test plants with a small sprayer. After the application, the test plants were grown in the greenhouse for days, and the herbicidal activity was then examined. The results are given in Table 2.

TABLE 2

| Examined Compound | Dosage (g/ha) | Herbicidal Activity | | |
|---|---|---|---|---|
| | | AE | IB | SM |
| Cinidon-ethyl | 80 | 3 | 3 | 3 |
| Glufosinate-ammonium | 280 | 3 | 3 | 3 |
| Cinidon-ethyl and Glufosinate-ammonium | 80 + 280 | 9 | 9 | 9 |

EFFECT OF THE INVENTION

A wide variety of weeds in corn fields, soybean fields, wheat fields, barley fields, oat fields, rye fields, rice fields, paddy fields or the like, can be controlled with selectivity by using the present inventive compositions.

What is claimed is:
1. A herbicidal composition, which comprises a synergistically effective amount of (i) at least one compound selected from the group consisting of N-(phosphonomethyl)glycine, a salt thereof, and ammonium-DL-homoalanin-4-yl(methyl)phosphinate; and (ii) ethyl 2-chloro-3-[2-chloro-5-(1,3-dioxo-4,5,6,7-tetrahydroisoindolin-2-yl)phenyl]acrylate as active ingredients.

2. The herbicidal composition according to claim 1, wherein the weight ratio of component (i) to component (ii) in said composition is from about 0.5:1 to 500:1.

3. The herbicidal composition according to claim 1, wherein the weight ratio of component (i) to component (ii) in said composition is from about 2:1 to 100:1.

4. The herbicidal composition according to claim 1, wherein component (i) is N-(phosphonomethyl)glycine or a salt thereof, and the weight ratio of component (i) to component (ii) in said composition is from about 7:1 to 56:1.

5. The herbicidal composition according to claim 1, wherein component (i) is ammonium-DL-homoalanin-4-yl(methyl)-phosphinate, and the weight ratio of component (i) to component (ii) in said composition is from about 3.5:1 to 28:1.

6. A method for controlling weeds, which comprises applying a synergistically herbicidally effective amount of (i) at least one compound selected from the group consisting of N-(phosphonomethyl)glycine, a salt thereof and ammonium-DL-homoalanin-4-yl(methyl)phosphinate; and (ii) ethyl 2-chloro-3-[2-chloro-5-(1,3-dioxo-4,5,6,7-tetrahydroisoindolin-2-yl)phenyl]acrylate to said weeds or place in which said weeds grow or can grow.

7. The method for controlling weeds according to claim 6, wherein the weight ratio of component (i) to component (ii) being applied to said weeds or said place in which said weeds grow or can grow is from about 0.5:1 to 500:1.

8. The method for controlling weeds according to claim 6, wherein a total amount of component (i) and (ii) being applied to said weeds or said place in which said weeds grow or can grow is from about 100 to 10,000 g per hectare.

9. The method according to claim 6, wherein the weight ratio of component (i) to component (ii) is from about 2:1 to 100:1.

10. The method according to claim 6, wherein component (i) is N-(phosphonomethyl)glycine or a salt thereof, and the weight ratio of component (i) to component (ii) is from about 7:1 to 56:1.

11. The method according to claim 6, wherein component (i) is ammonium-DL-homoalanin-4-yl(methyl)-phosphinate, and the weight ratio of component (i) to component (ii) is from about 3.5:1 to 28:1.

12. The method according to claim 6, wherein a total amount of component (i) and (ii) is from about 200 to 2,000 g per hectare.

* * * * *